United States Patent [19]

Samsel

[11] Patent Number: 5,231,771
[45] Date of Patent: Aug. 3, 1993

[54] VACUUM DRYING METHOD FOR METALLIC WORKPIECES

[75] Inventor: W. Scott Samsel, Bristol, Conn.

[73] Assignee: United States Surgical Corporation, Norwalk, Conn.

[21] Appl. No.: 953,552

[22] Filed: Sep. 29, 1992

[51] Int. Cl.⁵ .................................... F28B 5/04
[52] U.S. Cl. .......................... 34/15; 34/92
[58] Field of Search ............ 34/15, 92, 104, 107

[56] References Cited

U.S. PATENT DOCUMENTS 3,983,637  10/1976  Johnson .................... 34/15

FOREIGN PATENT DOCUMENTS 3-80869  4/1991  Japan .

Primary Examiner—Henry A. Bennet
Attorney, Agent, or Firm—Thomas R. Bremer; Peter G. Dilworth; Rocco S. Barrese

[57] ABSTRACT

Metallic workpieces, such as surgical needles, which have been washed with an aqueous solution are dried by subjecting the workpieces to heat and reduced pressure in the presence of an inert gas.

31 Claims, No Drawings

VACUUM DRYING METHOD FOR METALLIC WORKPIECES

FIELD OF THE INVENTION

The present invention relates generally to methods for drying metallic workpieces. More specifically, this invention relates to methods for drying surgical needles which have been washed with an aqueous solution.

BACKGROUND OF THE INVENTION

Metallic workpieces, such as surgical needles, are frequently subjected to various operations, such as grinding, polishing, bending and drilling. These operations, whether performed manually or in an automated manner, will normally deposit debris, such as filings, ground metal or particles of grinding material, on the workpiece. In addition, grease or other dirt either from the hands of the operator or, for example, from lubricants applied to the machinery on which the piece is worked, may also be deposited on the workpiece. Accordingly, it is normally necessary to clean the workpiece after it has undergone one or more processing steps.

Freon is one solvent which has been used to clean metallic workpieces. Recently, however, environmental concerns in connection with Freon and other fluorocarbons has led to the use of aqueous solvents for cleaning metallic workpieces. Extended contact of a metallic workpiece with an aqueous environment, however, may result in oxidation of the metal, causing roughness, loss of lustre or pitting of the workpiece. This is particularly true where the workpiece has sharpened edges, polished surfaces or a sharp point as is the case with a surgical needle.

It is therefore an object of the present invention to provide methods for drying metallic workpieces which have been washed with an aqueous solvent.

SUMMARY OF THE INVENTION

In accordance with the methods of the present invention, a metallic workpiece which has been washed with an aqueous solution is dried by placing the workpiece within a chamber and initially preheating the chamber by energizing at least one heater. During preheating an inert gas is introduced into the chamber and the chamber is vented, creating a flow of the inert gas through the chamber. Once the chamber is preheated, the chamber is evacuated while an elevated temperature is maintained within the chamber. Inert gas is then introduced into the chamber and the chamber is vented, whereby the chamber is purged and cooling of the chamber begins. The dried workpieces may then be removed from the chamber.

DESCRIPTION OF THE PREFERRED EMBODIMENTS

While the present invention will be described with respect to surgical needles, it should be understood that any metallic workpieces which have been washed with an aqueous solution can be dried in accordance with this invention. The nature of the aqueous solution employed to wash the needles is not critical to this invention. In addition, the present process may be employed to dry single workpieces or a plurality of workpieces simultaneously.

Initially, the needles are placed within a chamber. Preferably, the needles are pre-loaded onto a holder and then the holder having the needles thereon is placed into the chamber. Most preferably, the holder positions the needles such that there is space of from about 2 to 6 inches between the bottom of the chamber and the needles to be dried to allow the circulation of warm gas around the needles. Additionally, a particularly useful holder will contact a minimum amount of the surface of the needles in order to minimize the possibility of trapping moisture between the needle and the holder.

Once the needles are positioned within the chamber, the chamber is preheated by energizing one or more heaters. Any type of conventional heater may be used. For example, a radiant heater located within the chamber can be used to preheat the chamber. Alternatively, a convective heater located outside the chamber and blowers may be used to move heated gas into the chamber. In an alternative embodiment, the pressure within the chamber is reduced prior to preheating. In this case, radiant heaters are preferred for preheating due to their improved efficiency compared to convective heaters in reduced pressure environments.

To provide uniform heating, more than one radiant heater may be located within the chamber, for example, one heater above the needles and one heater below the needles. Additional heaters may be provided along the sides of the chamber. Depending on the size of the chamber, fans or baffles may be included in the chamber to assist in even distribution of the heat. Where external heaters are used, blowers may deliver gas to a plurality of inlet ports at various locations within the chamber, the distribution of the inlet ports providing an even distribution of heat.

The chamber is preheated to a temperature of from about 100° F. to about 400° F. The duration of the preheating step will depend on the size of the chamber and the temperature to which the chamber is preheated, but will normally range from about 1 minute to about 10 minutes. Any residual heat from a previous drying cycle will tend to shorten the time required for the preheating step.

Gas may be introduced to the chamber during the preheating step. Preferably the gas will be an inert gas; that is, a gas which will not produce any substantial chemical reaction with the needle or any residual aqueous solution thereon over the time period of the drying process. Suitable inert gases include nitrogen and argon. If a reactive gas is used, it may be mixed with an inert diluting gas prior to introduction into the chamber. Most preferred are gases which can be provided with little to no moisture contained therein. Nitrogen gas is one such gas commonly available. The rate at which the gas is introduced into the chamber will depend upon the diameter of the inlet and vent lines. Generally, the flow rate of gas into the chamber should not be sufficient to displace the workpieces being dried. Thus, where the needles are securely held in a holder, higher flow rates can be used and the overall drying cycle time reduced. However, when the workpieces are not held in place, lower flow rates may be required to avoid movement of the workpieces within the chamber. This is particularly true with respect to smaller size surgical needles. Baffles or diffusers may be used to avoid movement of the needles during the introduction of gas.

Venting of the chamber may be provided simultaneously with the introduction of gas. This simultaneous venting and gas introduction will provide a flow of gas through the chamber to begin removal of moisture during preheating. In particularly useful embodiments, the introduction of gas and the venting will be through ports positioned at opposite locations within the chamber. For example, one or more gas introduction ports may be located at the bottom of the chamber and one or more vents may be located at the top of the chamber. Alternatively, the gas introduction port or ports and vent or vents may be located on opposite sides of the chamber. The location of gas inlet ports and vents may be distributed to provide a substantially uniform flow of gas through the chamber.

Once the atmosphere within the chamber has been preheated to a predetermined temperature, the flow of gas into the chamber and venting can be stopped, and the pressure within the chamber is reduced. Any conventional means may be employed to reduce the pressure within the chamber such as, for example, a vacuum pump. Preferably, a vacuum pump in combination with an adjustable vacuum regulator is used to evacuate the chamber. The pressure within the chamber is reduced to below about 700 torr. Preferably the pressure is reduced to somewhere between 1 and 400 torr. Most preferably, the pressure is reduced to between 1 and 100 torr.

During evacuation, the heaters may remain energized, thereby maintaining the temperature achieved during preheating or further raising the temperature within the chamber. During evacuation the temperature within the chamber may range from about 100° F. By providing insulation on the walls of the chamber, the need to keep the heaters energized during all or part of the evacuation step may be avoided. The duration of the evacuation step will depend upon the pressure to which the chamber is evacuated, but will generally last anywhere from about 1 minute to about 10 minutes.

Once a predetermined pressure is achieved within the chamber, the chamber may optionally be maintained at that pressure for a period of time of up to 6 hours. To easily carry out this optional holding step, the chamber is preferably constructed so as to be completely sealable. For example, the door to the chamber should be provided with an air tight seal and all gas introduction ports, venting ports and ports leading to the evacuation means should be sealable.

The length of time the chamber is held in the evacuated state will normally vary inversely with the pressure to which the chamber is evacuated. For example, when the chamber is evacuated to 400-500 torr, the chamber may be held at this pressure for 60 minutes. When, however, the chamber is evacuated to 100 torr or less, no holding period may be required.

When the holding period, if any, is over, or when the chamber reaches a predetermined pressure, gas is introduced into the chamber. The gas introduced after the evacuation step may be the same or different as the gas introduced during preheating. Preferably, the gas introduced after evacuation is an inert gas, such as nitrogen gas. The evacuation apparatus is de-activated during this gas introduction and is preferably isolated from the chamber. As with the gas introduced during preheating, the gas introduced after evacuation preferably contains a controlled amount of moisture, most preferably little to none.

Gas is introduced into the chamber until the pressure therein is at or slightly over atmospheric pressure, preferably a pressure of up to about 800 torr. Where pressures in excess of atmospheric pressure are achieved, the chamber may be vented to permit a small flow of gas out to purge the chamber and assist in cool down of the chamber. During this venting period, the introduction of gas into the chamber may be continued to establish a flow of gas through the chamber, thereby removing moisture from the environment surrounding the needles.

Where the gas employed is reactive, precautions such as purge steps and scrubbing steps should be added.

Ultimately, the needles are removed from the chamber. The needles may be allowed to cool within the chamber prior to removal. Preferably, the needles are removed and another batch of needles loaded into the chamber before any significant cool down occurs, thereby taking advantage of any residual heat within the chamber and increasing the efficiency of the process.

The overall time which will elapse for the drying process of the present invention will depend upon a number of factors including the temperature and pressure achieved within the chamber, but typically the duration of the entire process will range from 3 minutes to 30 minutes.

What is claimed is:

1. A method for drying a metallic workpiece which has been washed with an aqueous solution, the method comprising:
   placing the workpiece within a chamber;
   preheating the chamber;
   introducing an inert gas into the chamber during said preheating step;
   venting the chamber during said preheating step whereby a flow of the inert gas through the chamber is achieved;
   reducing the pressure within the chamber while maintaining an elevated temperature within the chamber;
   after a predetermined reduced pressure is attained within the chamber, raising the pressure in the chamber by introducing an inert gas into the chamber; and
   removing the workpiece from the chamber.

2. A method as in claim 1 further comprising the step of placing the workpiece on a holder which holder carrying the workpiece is placed within the chamber.

3. A method as in claim 2 wherein said holder positions the workpiece above the bottom of the chamber.

4. A method as in claim 3 wherein said preheating step comprises energizing heaters positioned above and below the workpiece.

5. A method as in claim 1 wherein said preheating step raises the temperature within the chamber to a temperature between about 100° F. and about 400° F.

6. A method as in claim 1 wherein said inert gas introduced during said preheating step is the same as the inert gas introduced to raise the pressure within the chamber.

7. A method as in claim 6 wherein said inert gas is selected from the group consisting of argon and nitrogen.

8. A method as in claim 1 wherein the flow of gas achieved by said introduction of gas and said venting is across the distance of a full dimension of the chamber.

9. A method as in claim 1 wherein the pressure within the chamber is reduced to a pressure between about 1 and about 700 torr.

10. A method as in claim 9 wherein the pressure is reduced to a pressure between about 1 and 100 torr.

11. A method as in claim 1 wherein the pressure within the chamber is raised to a pressure up to about 800 torr by the introduction of gas.

12. A method as in claim 1 further comprising the step of maintaining the temperature within the chamber in the range of from about 100° F. to about 400° F. while carrying out the step of reducing the pressure within the chamber.

13. A method as in claim 1 further comprising the step of maintaining the chamber at an elevated temperature and reduced pressure for a period of up to 6 hours prior to said pressure raising step.

14. A method as in claim 11 further comprising the step of venting said chamber after said pressure raising step whereby a flow of gas is achieved out of the chamber and moisture contained with the chamber is removed therefrom.

15. A method as in claim 1 further comprising the step of allowing said workpiece to cool prior to said removing step.

16. A method as in claim 1 wherein said workpiece is a surgical needle.

17. A method for drying a surgical needle comprising:
   placing the needle within a chamber;
   preheating the chamber;
   introducing an inert gas into the chamber during said preheating step;
   venting the chamber during said preheating step whereby a flow of the inert gas through the chamber is achieved;
   reducing the pressure within the chamber while maintaining an elevated temperature within the chamber;
   after a predetermined reduced pressure is attained within the chamber, raising the pressure in the chamber by introducing an inert gas into the chamber; and
   removing the needle from the chamber.

18. A method as in claim 17 further comprising the step of placing the needle on a holder which holder carrying the needle is placed within the chamber.

19. A method as in claim 18 wherein said holder positions the needle above the bottom of the chamber.

20. A method as in claim 19 wherein said preheating step comprises energizing heaters positioned above and below the needle.

21. A method as in claim 17 wherein said preheating step raises the temperature within the chamber to a temperature between about 100° F. and about 400° F.

22. A method as in claim 17 wherein said inert gas introduced during said preheating step is the same as the inert gas introduced to raise the pressure within the chamber.

23. A method as in claim 22 wherein said inert gas is selected from the group consisting of argon and nitrogen.

24. A method as in claim 17 wherein the flow of gas achieved by said introduction of gas and said venting is across the distance of a full dimension of the chamber.

25. A method as in claim 17 wherein the pressure within the chamber is reduced to a pressure between about 1 and about 700 torr.

26. A method as in claim 25 wherein the pressure is reduced to a pressure between about 1 and 100 torr.

27. A method as in claim 17 wherein the pressure within the chamber is raised to a pressure up to about 800 torr by the introduction of gas.

28. A method as in claim 17 further comprising the step of maintaining the temperature within the chamber in the range of from about 100° F. to about 400° F. while carrying out the step of reducing the pressure within the chamber.

29. A method as in claim 17 further comprising the step of maintaining the chamber at an elevated temperature and reduced pressure for a period of up to 6 hours prior to said pressure raising step.

30. A method as in claim 27 further comprising the step of venting said chamber after said pressure raising step whereby a flow of gas is achieved out of the chamber and moisture contained with the chamber is removed therefrom.

31. A method as in claim 17 further comprising the step of allowing said needle to cool prior to said removing step.

* * * * *